(12) United States Patent
Lin

(10) Patent No.: US 6,536,910 B2
(45) Date of Patent: Mar. 25, 2003

(54) VAPOR GENERATING LAMPSHADE APPARATUS

(76) Inventor: Chun-Horng Lin, 19222 Tranbarber St., Rowland Heights, CA (US) 91748

( * ) Notice: Subject to any disclaimer, the term of this patent is extended or adjusted under 35 U.S.C. 154(b) by 0 days.

(21) Appl. No.: 09/933,182

(22) Filed: Aug. 21, 2001

(65) Prior Publication Data

US 2003/0039115 A1 Feb. 27, 2003

(51) Int. Cl.[7] ................................................ F21V 33/00
(52) U.S. Cl. ........................ 362/96; 362/351; 40/406; 40/407
(58) Field of Search ..................... 362/96, 351, 808; 446/24; 40/406, 407

(56) References Cited

U.S. PATENT DOCUMENTS 3,537,709 A * 11/1970 O'Connell .................. 273/161
5,678,918 A * 10/1997 Lin .............................. 362/96

* cited by examiner

Primary Examiner—Sandra O'Shea
Assistant Examiner—Ronald E. DelGizzi
(74) Attorney, Agent, or Firm—Rosenberg, Klein & Lee

(57) ABSTRACT

Disclosed herein is a tender mood creating lampshade equipped with a fog generator which oscillates at a supersonic frequency thereby vaporizing particles of liquidal perfume or equivalents in a liquid container into foggy state and diffusing in the air through an ornamental idol to create a tender mood in the surroundings.

9 Claims, 6 Drawing Sheets

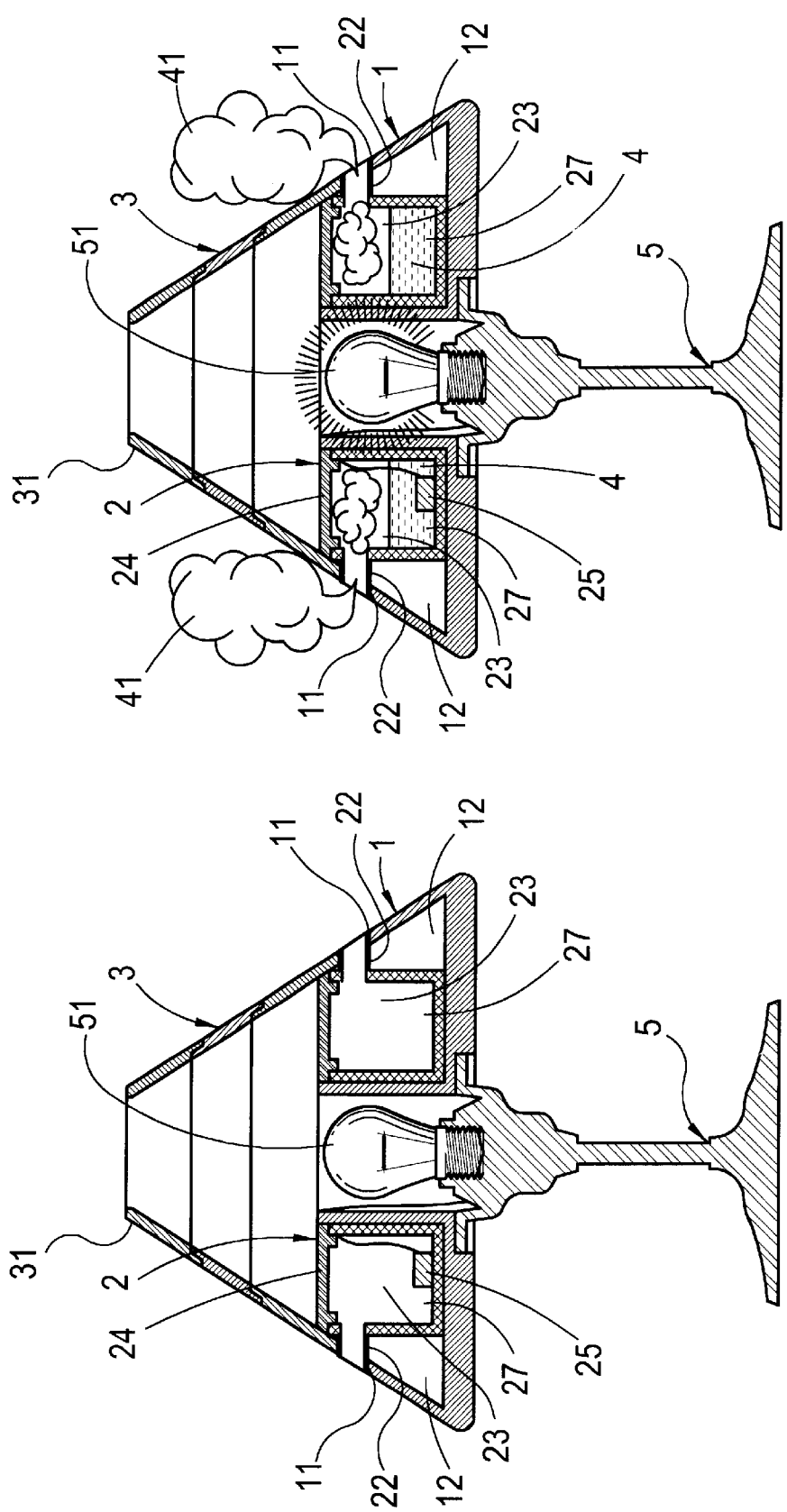

VAPOR GENERATING LAMPSHADE APPARATUS

BACKGROUND OF THE INVENTION

1. Field of the invention

The present invention relates to a tender mood creating lampshade, and more particularly, to a lampshade having a fog generator which oscillates at a supersonic frequency thereby vaporizing particles of liquidal perfume in a container into foggy state and diffusing in the air to create a tender mood in the surroundings.

2. Description of the Prior Art

In the bygone time, the aim of installing a lamp is only for lighting the surroundings. However, nowadays it functions not only for lighting but also for decoration as well, and the latter may play more important roll than the former.

There are a lot of so-called mood improving luminaries whose design lays emphasis on static beauty of construction materials and luster of colar. However, in the present days, it seems necessary to call for one more step advanced improvement for a lampshade to exhibit a dynamically vivid mood in addition to its static beauty.

SUMMARY OF THE INVENTION

In effort for coping with this situation, researches and developments are being carried out for a long time by the inventor of the present invention, and finally came out with a tender mood ereating lampshade of the present invention.

It is an object of the present invention to provide a tender mood creating lampshade having a liquid container containing a perfume therein and a fog generator which oscillates at a supersonic frequency thereby vaporizing particles of the liquidal perfume into foggy state and diffusing in the air.

It is another object of the present invention to provide a tender mood creating lampshade that ornamental carvings and an ornament are attachable to the lampshade for enhancing its beauty.

To achieve the above mentioned objects, the tender mood creating lampshade of the present invention comprises an slot base, a liquid container, a shade, and a fog generator. The slot base has several recessed breaches formed around an upper fringe of the slot opening thereof. The liquid container has several connecting tubes attached to its vertical wall at a proper height mating with corresponding breaches around the upper fringe of the slat opening, the slot opening is covered with a lid such that an inner part of the liquid container is formed into a closed cavity. The shade is mounted on the upper fringe of the base slot and the fog generator is immersed in the liquid of the liquid container.

Meanwhile, the shade may be composed of several layers of sub-shade, and the lampshade may be provided with a stand at the bottom of the slot base.

In the present invention the liquid container may be formed of a plurality of sub-containers each having a connecting tube mating with corresponding breach on the slot base respectively.

For ornamental purpose, an ornament in the form of an auspicious animal or bird idol is provided at the exit of the connecting tube, and the outer surface of the shade may be formed into an artistic carving or a printed pattern for butification of lampshade's outer appearance.

BRIEF DESCRIPTION OF THE DRAWINGS

For fuller understanding of the nature and object of the invention, reference should be made to the following detailed description taken in conjunction with the accompanying drawings in which:

FIGS. 3(A) and 3(B) are cross sectional views of the lampshade equipped with a stand in a first embodiment of the present invention;

DETAILED DESCRIPTION OF THE PREFERRED EMBODIMENT

Figure 1:
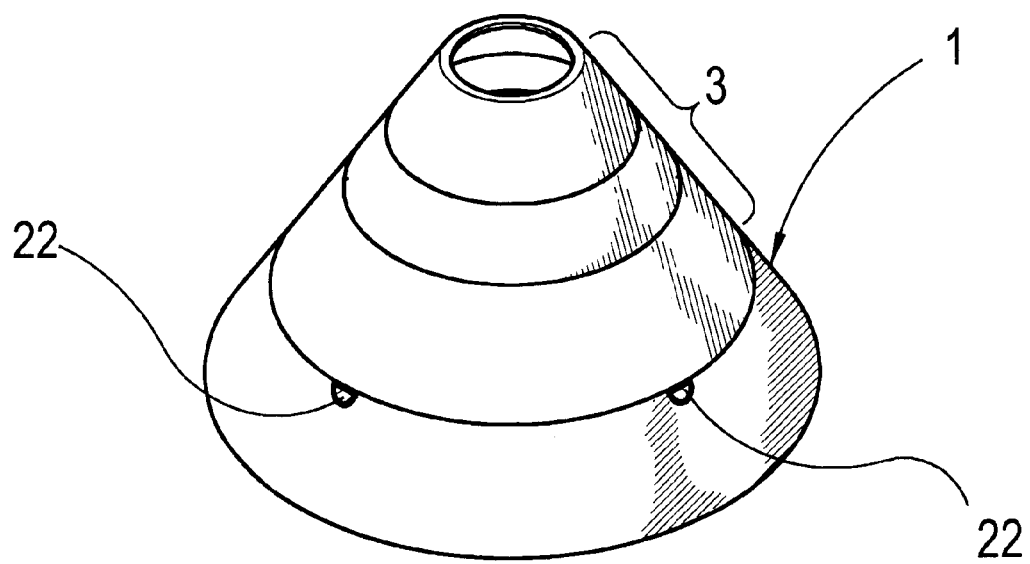
FIG. 1 is a three dimensional view of the tender mood creating lampshade of the present invention.
Figure 2:
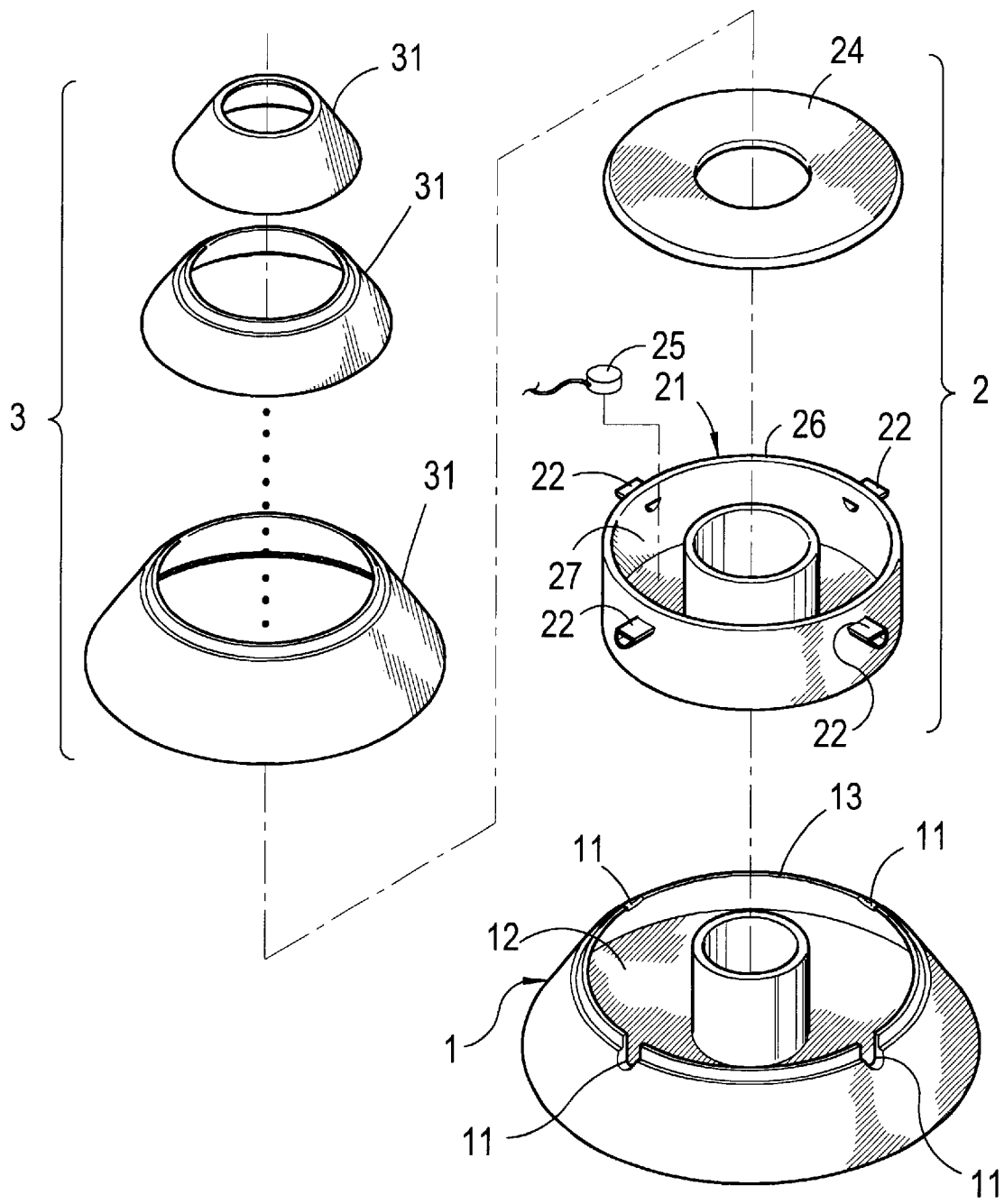
FIG. 2 is an exploded view showing component parts of the lampshade of the present invention.

Referring simultaneously to FIG. 1 and FIG. 2, where FIG. 1 is a three dimensional view, and FIG. 2 is an exploded view of the present invention, respectively. The lampshade of the present invention generally comprises a slot base 1, a liquid container 2, a shade 3, and a fog generator 25. The slot base 1 has several recessed breaches 11 formed around an upper fringe 13 of the slot opening 26 thereof. The liquid container 2 has several connecting tubes 22 attached to its vertical wall at a proper height so as to mate with the corresponding breaches 11. The slot opening 26 is covered with a lid 24 such that an inner part 27 of the liquid container 2 is formed into a closed cavity 23 (referring to FIGS. 3(A), 3(B)). The shade 3, composed of several layers of sub-shade 31, is to be covered on the upper fringe 13 of the slot base 1.

Referring simultaneously to FIG. 3(A) and FIG. 3(B), where both drawings are cross sectional views for a first embodiment of the present invention, wherein the lampshade is equipped with a stand 5. An electric bulb 51 installed in the lampshade will emit ligh rays when supplied by electricity. A liquid 4, such as a perfume is filled in the inner part 27 of the liquid container 2. The fog generator 25 in the closed cavity 13 of the liquid container 2 vaporizes the particles of the liquid 4 when it is connected to a power source and oscillates at a supersonic frequency such that the vaporized particles of the liquid 4 are diffused in the air in a foggy state 41 and egressed out of the closed cavity 23 after the vaporized particles are saturated therein.

Figure 4A:
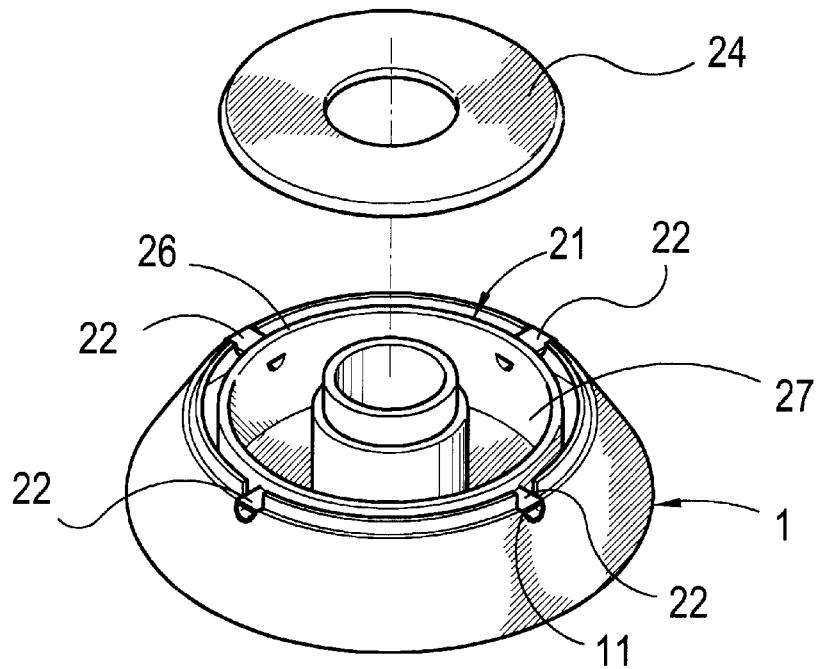
FIG. 4(A) is an illustrative view showing the assembly of the slot base with the liquid container in a first embodiment of the present invention.
Figure 4B:
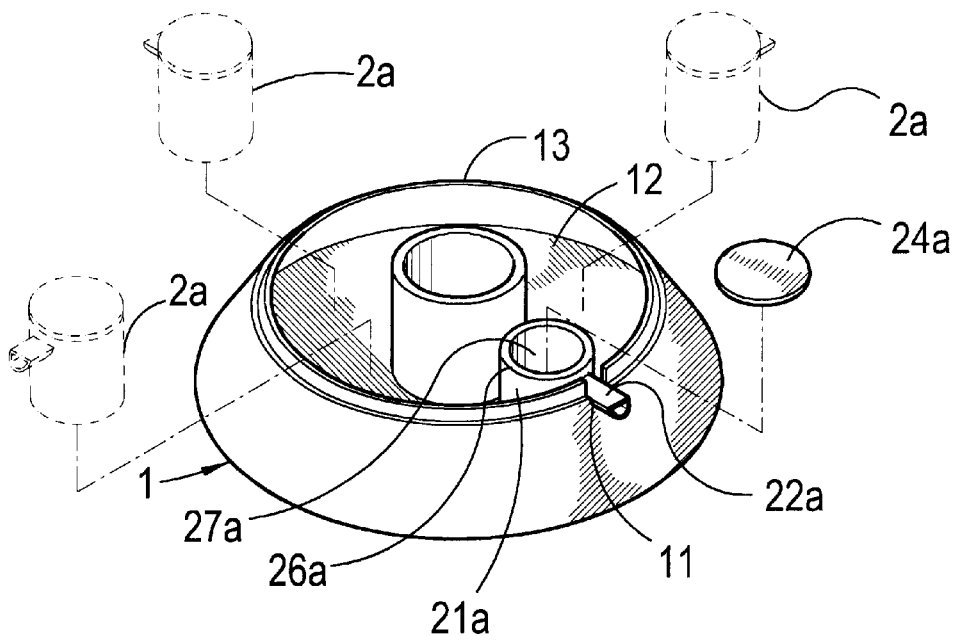
FIG. 4(B) is an illustrative view showing the assembly of the slot base with the liquid container in a second embodiment of the present invention.

Referring simultaneously to FIG. 4(A) and FIG. 4(B), where FIG. 4(A) is an illustrative view showing the assembly of the slot base 1 with the liquid container in a first embodiment, and FIG. 4(b) is a second embodiment of the present invention thereof. As shown in FIG. 4(A), the liquid container 2 is formed in a slot 12 of the slot base 1, whereas in FIG. 4(B), a plurality of sub-liquid containers 2a are formed in the slot base 1. An opening 26a of each sub-container 2a has its own lid 24a to cover on an inner part 27a of each sub-container 2a. Besides, a connecting tube 22a is provided for each sub-container 2a on its wall 21a, and is mating with the corresponding recessed breach 11.

Figure 5A:
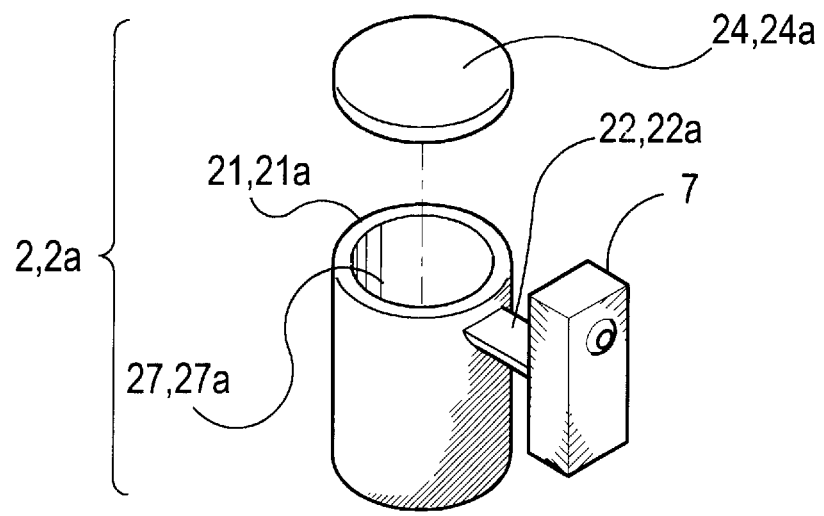
FIG. 5(A) is an illustrative view for a third embodiment of the present invention.

Referring to FIG. 5(A), an illustrative view for a third embodiment of the present invention, as shown in FIG. 5(A), the connecting tube 22 or 22a on the slot wall 21 or 21a for the liquid container 2 or 2a has an ornament 7 disposed at its exit thereof. In this version the user is allowed to replace the ornament 7 together with the liquid container 2 or 2a for the two are formed in pair.

Figure 5B:
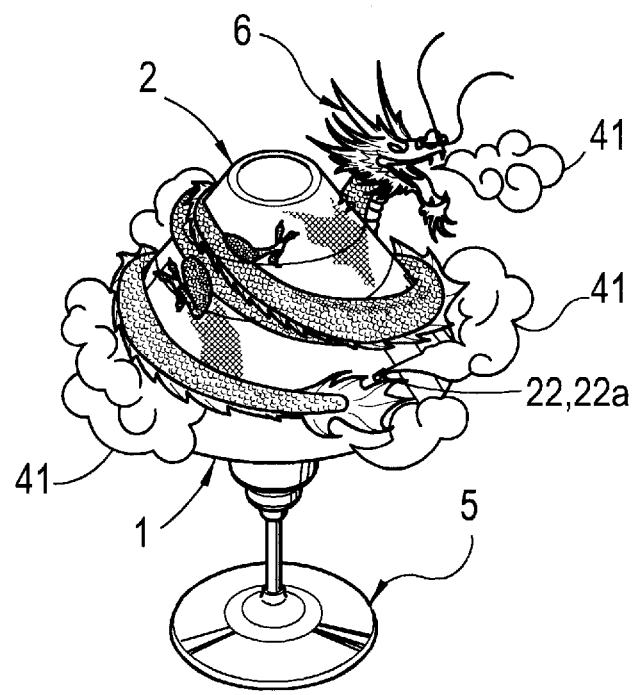
FIG. 5(B) is an illustrative view for a fourth embodiment of the present invention having sub-shade portions defining a predetermined ornamental configuration.

Referring to FIG. 5(B), an illustrative view for a fourth embodiment of the present invention, as shown in, FIG. 5(B), the shade 3 is formed of multiple layers of sub-shade 31, and the outer surface thereof is formed into artistic carving, and an auspicious animal or bird idol 6 is provided at the exit of the connecting tube 22 or 22a such that the foggy vapor 41 may be egressed out of the idol's mouth, nose, or eyes thereby creating a vivid and interesting mood.

Figure 6A:
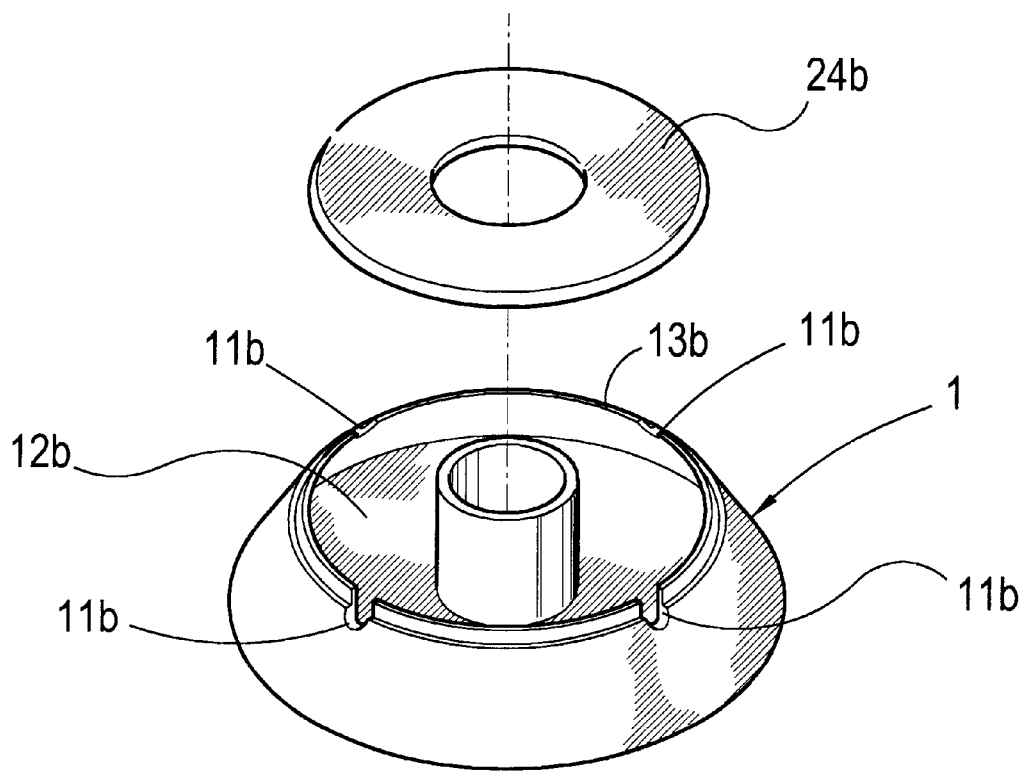
FIG. 6(A) is an illustrative view for a fifth embodiment of the present invention.
Figure 6B:
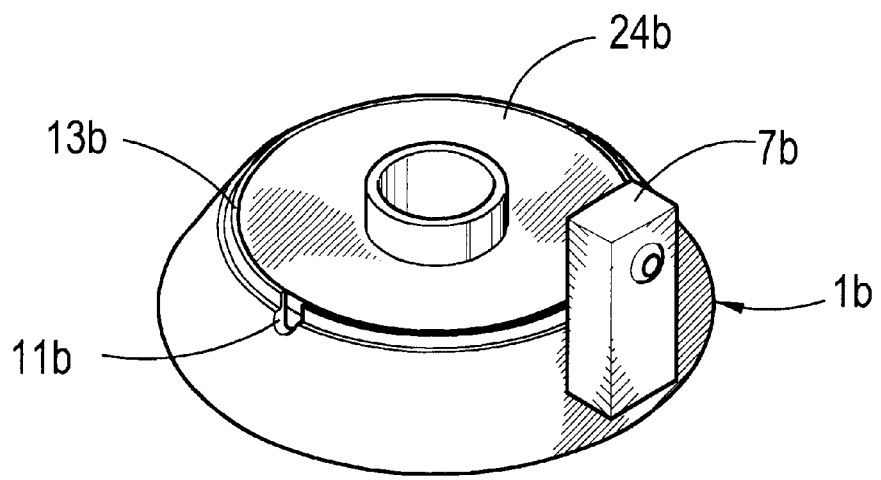
FIG. 6(B) is an illustrative view of a sixth embodiment of the present invention similar to the embodiment shown in FIG. 6(A), but equipped with an ornament.

Referring to FIG. 6(A) and FIG. 6(B), FIG. 6(A) is an illustrative view for a fifth embodiment of the present invention, and FIG. 6(B) is a view of an embodiment similar to that shown in FIG. 6(A), but equipped with an ornament 7b. In another form of the structure, the liquid container 2 or sub-container 2a is omitted, and instead, it is replaced by a slot 12b of a slot base 1b, and several recessed breaches 11b are formed around an upper fringe 13b of the wall of the slot base 12b thereof, at a proper height. A lid 24b is covered on an upper fringe 13b of the slot base 1b. An ornament 7b is provided for each breach 11. The principle of operation is similar to that described above. The particles of the liquid 4 in the slot 12b are vaporized by the fog generator 25 oscillating at a supersonic frequency and diffused outside of the lampshade in a foggy state 41.

It emerges from the description of the above embodiments that the invention has several noteworthy advantages, in particular:

1. A plurality of liquidal substances can be filled in the liquid container so as to produce various kinds of fogs.
2. An ornament provided at the exit of each connecting tube can be replaced together with the corresponding liquid container or sub-container so as to meet the taste of the individual user.
3. Variety of carving patterns may be formed on the shade to fit for specific environmental requirements, such as the religious chapel and cathedral, or the recreation establishment.

Many changes and modifications in the above described embodiment of the invention can, of course, be carried out without departing from the scope thereof. Accordingly, to promote the progress in science and the useful arts, the invention is disclosed and is intended to be limited only by the scope of the appended claims.

What is claimed is:

1. A mood creating lampshade comprising:
    a slot base having a plurality of recessed breaches formed around an upper fringe of a slot opening;
    a liquid container having a plurality of connecting tubes extending from a vertical wall thereof to mate with a corresponding one of said breaches, the slot opening being covered with a lid to define a closed cavity at an inner part of said liquid container;
    a shade; and
    a fog generator;
    said fog generator being immersible in a liquid in said liquid container which is disposed on said slot base, and said shade being disposed to cover the upper fringe of said slot base.

2. The lampshade of claim 1, wherein said shade includes a plurality of layers of sub-shade.

3. The lampshade of claim 1, wherein said lampshade is provided with a stand at the bottom of said slot base.

4. The lampshade of claim 1, wherein said liquid container is formed of a plurality of sub-containers.

5. The lampshade of claim 4, wherein each of said sub-containers has a connecting tube mating with a corresponding one of said breaches on the slot base.

6. The lampshade of claim 1, wherein an ornament is provided at an outlet of said connecting tube.

7. The lampshade of claim 2, wherein the outer surface of said shade is formed into an artistic carving or a printed pattern.

8. A mood creating lampshade comprising:
    a slot base including a wall defining a slot having a plurality of recessed breaches formed around an upper fringe of said wall of said slot base, a lid covering said upper fringe of said slot base so as to form a closed cavity therein;
    a shade; and
    a fog generator;
    said fog generator being immersible in a liquid in said closed cavity formed on said slot base, and said shade being disposed to cover the upper fringe of said slot base.

9. The lampshade of claim 8, wherein each said recessed breach formed on said slot base is provided with an ornament attached thereto.

* * * * *